United States Patent [19]
Nakamura et al.

[11] 3,992,174
[45] Nov. 16, 1976

[54] SPECIMEN CAPSULE AND PROCESS FOR GAS CHROMATOGRAPHY

[75] Inventors: Sigeru Nakamura; Mitsuru Taguchi, both of Yokohama; Satoru Naniwada, Hoya; Naoki Ohguri, Hachioji, all of Japan

[73] Assignees: Japan Analytical Industry Co. Ltd.; Showa Denko Kabushiki Kaisha, both of Tokyo, Japan

[22] Filed: Dec. 13, 1974

[21] Appl. No.: 532,537

Related U.S. Application Data

[62] Division of Ser. No. 337,712, March 2, 1973, Pat. No. 3,879,181.

[30] Foreign Application Priority Data

| Mar. 9, 1972 | Japan | 47-24250 |
| Mar. 9, 1972 | Japan | 47-24251 |
| May 8, 1972 | Japan | 47-44583 |

[52] U.S. Cl. .................................... 55/67; 23/232 C
[51] Int. Cl.² .......................................... B01D 15/08
[58] Field of Search ............... 55/67, 197, 386; 23/230 PC, 232 C, 232 E; 206/.7, 225, 226, 532, 528

[56] References Cited
UNITED STATES PATENTS

| 3,168,377 | 2/1965 | Williams, Jr. | 23/230 PC |
| 3,468,635 | 9/1969 | Richmond | 23/230 PC |
| 3,672,844 | 6/1972 | Long | 23/230 PC |
| 3,684,454 | 8/1972 | Martin et al. | 23/230 PC |

*Primary Examiner*—John Adee
*Attorney, Agent, or Firm*—Kurt Kelman

[57] ABSTRACT

For use in gas chromatograph, there is provided a specimen capsule which has a sample wrapped in a foil or net of ferromagnetic metal. Also provided is a process for gas chromatography which comprises the steps of placing the specimen capsule in the vaporizer of the gas chromatograph, vaporizing the sample by means of alternative current induction and conducting necessary analysis on the resultant gases.

2 Claims, 5 Drawing Figures

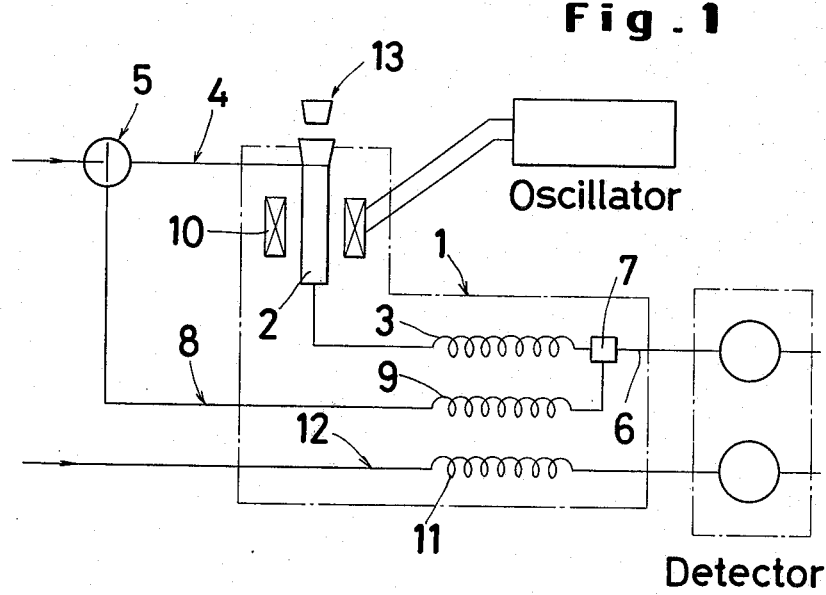
Fig.1
Fig.2 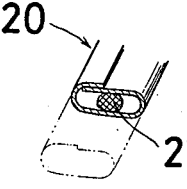 Fig.3 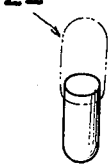 Fig.4 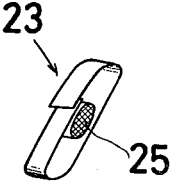 Fig.5 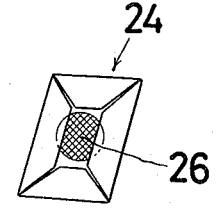

SPECIMEN CAPSULE AND PROCESS FOR GAS CHROMATOGRAPHY

This is a division of application Ser. No. 337,712, filed Mar. 2, 1973, now U.S. Pat. No. 3,879,181.

BACKGROUND OF THE INVENTION

This invention relates to improved pyrolysis gas chromatograph specimen capsules and a process for analysis using said specimen capsules.

Generally in gas chromatography, a sample to be analyzed is placed in a vaporizer and vaporized by heating or by pyrolysis; the vaporized components are swept by a carrier gas into a column filled with a column packing; the components of the sample vapour are carried through the column at different rates, which are governed by their partition coefficient between the gas phase and the stationary phase. They emerge from the end of the column at different times. Their presence in the emerging carrier gas is detected by chemical or physical means.

It is desirable that the flow of carrier gas through the column packing should be continued while the column is not in service, namely during the preparation period, so as to keep the column packing under fixed conditions and protect it against possible degradation. The carrier gas flows in different paths during the analysis period and during the preparation period. The switch of the path of flow is effected by means of a valve which is placed in the piping of the carrier gas. In most gas chromatographs, the column and the vaporizer are encased in a constant temperature oven so as to be kept at a predetermined temperature.

In the conventional pyrolysis gas chromatograph, the switching valve is placed between the vaporizer and the column and, during the analysis period, the vaporized components of the sample are carried by the carrier gas from the vaporizer to the analyzing column via the valve. It is, therefore, necessary that the valve be placed inside the constant temperature oven and maintained at the constant temperature, so that the sample is prevented from being condensed while passing through the valve.

The switching valve is required to incorporate compressible packings of a rubbery material which serve the purpose of sealing. To satisfy the purpose, these parts are made of heat-proof plastics such as, for example, Teflon. Even Teflon that has properties most suited to the purpose cannot withstand temperatures higher than 170° C. Thus, the temperature at which the constant temperature oven maintains the analyzing column is limited to the highest temperature that the aforementioned parts can withstand.

As concerns the injection of a sample into the vaporizer of the gas chromatograph, one known method accomplishes the injection by taking the sample in a micro-syringe, piercing the needle of this syringe through a rubber septum placed to close the entrance to the vaporizer and injecting the sample into the vaporizer.

When this method is applied to analyzing a volatile substance mingled with an involatile substance such as, for example, a solvent in a paint, the vaporization of the volatile component occurs first and requires a considerable length of time. Consequently, the sample tends to disperse prior to arrival at the column or it is found to be quite difficult to inject the entire sample to the column. There is another disadvantage that the residue of the sample cannot be extracted after completion of the analysis and it is left to contaminate the vaporizer and the column.

In other methods, the sample is injected into the vaporizer and thermally decomposed therein by the action of heat. There is known, for example, a method comprising the steps of having a sample solution deposited on the surface of a ferromagnetic metal wire about 0.6 mm in diameter and about 20 mm in length, drying the solution, inserting the wire into the vaporizer, exposing the wire to an alternate current magnetic field thereby inducing it to radiate heat and pyrolyzing the sample deposited on the wire. Since this method requires the sample to be deposited on the surface of the wire, the applicability of this method is limited to liquid samples or to solid samples which can be dissolved with solvents into solutions. The method is not applicable to solid insoluble samples. When a given solid sample is converted into a liquid sample by the use of a suitable solvent, the liquid sample is deposited on the wire and subsequently dried free of the solvent. From the practical point of view, however, thorough removal of the solvent content from the deposited sample is an impossibility. The gas produced from the deposited sample by pyrolysis, therefore, entrains the solvent component. This means that the chromatogram obtained by this method does not represent accurate analysis of the solid sample in the form thoroughly free from foreign matter.

The amount of the sample solution which is deposited on the wire must also be considered. Even if the solution to be deposited is the same, it is impossible to have exactly the same amount of solution deposited on all the wires in use. In the case of an excess of deposit, the recording of the results of analysis becomes impracticable because the peaks protrude over the edge of the chart paper. One same solution is deposited on a plurality of wires and the results of analysis conducted on each wire are recorded. Therefore, there is involved the troublesome work of making proper adjustment on each wire so that the peaks do not protrude over the edge of the chart paper. The amount of sample thus deposited on the wire is quite small. In the case of an operation in which mass spectrum is simultaneously performed using a mass spectrometer connected next to the gas chromatograph, therefore, the amount of the sample on the wire is not sufficient, making it impossible to carry out the mass spectrometric identification.

It is an object of this invention to provide a specimen capsule for use in a gas chromatograph, which permits accurate analysis of the volatile substances contained in high boiling substances and further to provide a process for analysis using the specimen capsule.

It is another object of the present invention to provide a specimen capsule for pyrolysis which eliminates the necessity of a solvent even where the sample to be analyzed happens to be a solid substance and which is also usable where the sample is a liquid substance and further to provide a process for the analysis using said specimen capsule.

Yet another object of this invention resides in providing a specimen containing a constant amount of sample.

SUMMARY OF THE INVENTION

This invention relates to a gas chromatograph specimen capsule having a sample wrapped in a foil or net of ferromagnetic metal. The specimen is then inserted in the vaporizer of the gas chromatograph and exposed to alternative current induction so that the ferromagnetic metal is heated to the extent of radiating heat and causing pyrolysis of the sample into a gaseous state. The gases thus produced from the sample are forwarded by the carrier gas into the column, wherein it is subjected to determination.

Other objects and characteristics of the present invention will become apparent from the description of the invention to be given in detail hereinafter with reference to the accompanying drawings.

BRIEF EXPLANATION OF THE DRAWING

FIG. 1 is a diagram illustrating one preferred embodiment of the system according to our U.S. Pat. No. 3,879,181.

FIGS. 2 to 5 are diagrams illustrating various specimen capsules according to the present invention in which the sample is wrapped in foils and nets made of ferromagnetic metal.

DETAILED DESCRIPTION OF THE INVENTION

The gas chromatograph will be explained with reference to FIG. 1.

In the diagram, 1 denotes a constant temperature oven, 2 a vaporizer disposed within the constant temperature oven and intended to vaporize or pyrolyze a sample and 3 an analyzing column disposed inside oven 1 next to heater compartment 2.

The vaporizer may be a quartz tube, for example, which has an opening to the outside of the constant temperature oven. The opening is kept closed at all times during operation with a septum 13. The septum 13 is removed when the specimen is inserted, when the interior of the vaporizer is cleaned or when the system is being prepared for analysis operation.

Pipe 4 for forwarding the carrier gas to the vaporizer 2 is provided outside the constant temperature oven with a switching valve 5. A pipe 6 for forwarding the carrier gas containing the separated components of the sample from the column 3 to a detector is provided inside the constant temperature oven 1 with a tee coupling 7. The aforesaid valve 5 and this tee coupling 7 are connected to each other by a pipe 8 which runs parallel to the vaporizer 2 and the column 3. Said vaporizer 2 is exposed to an alternate current magnetic induction field generated by oscillator 10. The pipe 8 is provided inside the constant temperature oven 1 with a dummy column 9 which is designed to balance the flow rate resistance.

The dummy column 9 is formed so as to provide the same amount of resistance to the passage of gas as the column 3. Consequently, possible difference in the volume of carrier gas being forwarded is minimized when the gas is flowing through the column and when it is flowing through this dummy column. This enhances the stability of operation of the entire system. The switching valve 5 has a structure of a three-way valve in which the path for the gas is shaped like the letter T. The forked coupling 7 has the structure of a T-shaped pipe.

The gases which may be used as the carrier gas in this invention are $N_2$, He, etc.

The manner in which the switching valve 5 is operated will be described in detail.

The valve 5 is a three-way valve of the kind frequently found in common use. FIG. 1 illustrates the valve 5 in the state which it assumes while the system is in the preparation period. During the preparation period, the carrier gas flows from the valve 5 to the tee coupling 7 via the pipe 8 which contains the dummy column 9. The flow of carrier gas is divided by the tee coupling 7 into two flows, one to the vaporizer 2 and the other to the concentration detector. By this flow of carrier gas, the column 9 has its column packing protected against possible degradation.

When the operation is to be switched to the analysis period, the three-way valve 5 is switched so that the carrier gas will flow through the pipe 4 and the flow of the gas to the pipe 8 will be stopped. Consequently, the carrier gas flows through the vaporizer 2 and enters the column 3 while entraining the vaporized components of the sample. In the column, the components are separated from one another by the column packing. Then, they are forwarded sequentially from this column and swept to the concentration detector.

An auxiliary piping containing a reference column 11 within the constant temperature oven is incorporated in the present gas chromatograph for the purpose of maintaining the accuracy of analysis at a high level.

Switching valve 5 is positioned in front of the vaporizer 2 and outside the constant temperature oven as already described. The vaporized sample is not allowed to pass through this valve under any condition. Therefore, the sample can be heated to as high a temperature as desired without reference to the kind of material of which the valve or its interior parts are made.

An explanation will now be given of the specimen capsule of this invention which permits accurate analysis selectively of the volatile substances in a mixture with non-volatile substances and to a process for analysis using the said specimen capsule.

FIGS. 2 to 5 are preferred embodiments of specimen capsules of the present invention. Referring to FIG. 2, 20 denotes a foil of ferromagnetic metal having a very small thickness of the order of 0.05 mm and 21 a sample which is wrapped in the foil. In this case, the sample is a solid substance.

In FIG. 3, a specimen capsule 22 is formed of a foil of ferromagnetic metal. This specimen capsule is suited for the analysis of a liquid sample. It can, of course, be applied to analysis of a solid sample.

FIG. 4 and FIG. 5 show samples 25 and 26 wrapped in foils 23 and 24 respectively. In the case of these two embodiments, the samples are limited to solid substances. The foils of ferromagnetic metal described in the above specimen capsules may be replaced by thin nets made of ferromagnetic metal. These nets, however, are not suitable for analysis of liquid samples.

Further, the specimen capsules may be prepared in structures combining foils and nets of ferromagnetic metal. A specimen capsule may be formed, for example, by placing a given sample on a foil of ferromagnetic metal and then covering the sample with a net.

The specimen capsules according to this invention are not limited to the shapes illustrated. Examples of other shapes the specimen capsules of this invention may assume include those formed by wrapping a foil of ferromagnetic metal around a given sample, by enclosing a sample with a net of ferromagnetic metal, by bending a foil or net mentioned above and inserting a sample inside the foil, and by placing a sample on a foil or net produced in the shape of a plate.

When any of the specimen capsules described above is mounted in the vaporizer of the gas chromatograph and then exposed to alternate current induction, the ferromagnetic metal piece is inductively heated and the sample is pyrolyzed into gaseous components which are dispersed throughout the interior of the vaporizer. By a known method previously described, the gases are swept by the carrier gas to the column. The components of the sample vapour are carried through the column at different rates, which are governed by their partition coefficient between gas phase and the stationary phase. They emerge from the end of the column at different times. Their presence in the emerging carrier gas is detected by chemical or physical means. As the ferromagnetic metal used in the specimen capsule of this type, iron, nickel, nickel-iron alloys, nickel-cobalt alloys, etc. may be used. Satisfactory selection has only to take into account the suitability to the kind of sample to be analyzed.

The specimen capsules and the process of analysis according to the present invention can use a solid sample in its unaltered form for the purpose of analysis and, therefore dispense with the treatment of dissolving a solid sample in a solvent which is indispensable for the conventionally known alternate current induction heating technique. Further, this invention has a great merit of permitting very easy preparation of specimen capsules containing any required sample, in addition to a decided advantage that it can be employed for the analysis of liquid samples.

We claim:

1. A process for analysis of a solid or liquid specimen, comprising the steps of wrapping said solid or liquid specimen in a foil or net of ferromagnetic metal to form a specimen capsule, inserting the specimen capsule into a vaporizer of a pyrolysis gas chromatograph, exposing the wrapped specimen to alternate current induction to cause the ferromagnetic metal to radiate heat and thereby vaporize the specimen wrapped therein, and introducing the vaporized components of the specimen into a column of the pyrolysis gas chromatograph.

2. A process according to claim 1, wherein the ferromagnetic metal is one member selected from the group consisting of iron, nickel, nickel-iron alloys and nickel-cobalt alloys.

* * * * *